(12) United States Patent
Bosma et al.

(10) Patent No.: US 7,240,635 B2
(45) Date of Patent: Jul. 10, 2007

(54) DEVICE AND A METHOD FOR SAMPLING OF MILK

(75) Inventors: Epke Bosma, Tumba (SE); Nils Erik Holmertz, Huddinge (SE)

(73) Assignee: DeLaval Holding AB, Tumba (SE)

( * ) Notice: Subject to any disclaimer, the term of this patent is extended or adjusted under 35 U.S.C. 154(b) by 117 days.

(21) Appl. No.: 10/512,011

(22) PCT Filed: Apr. 23, 2003

(86) PCT No.: PCT/SE03/00651

§ 371 (c)(1),
(2), (4) Date: Oct. 19, 2004

(87) PCT Pub. No.: WO03/090522

PCT Pub. Date: Nov. 6, 2003

(65) Prior Publication Data
US 2005/0223996 A1    Oct. 13, 2005

(30) Foreign Application Priority Data
Apr. 23, 2002   (SE) .................... 0201215

(51) Int. Cl.
*A01J 7/00* (2006.01)
(52) U.S. Cl. ................... 119/14.15; 119/14.08
(58) Field of Classification Search ............. 119/14.15, 119/14.14, 14.08, 14.03, 14.18
See application file for complete search history.

(56) References Cited

U.S. PATENT DOCUMENTS

| | | | | |
|---|---|---|---|---|
| 3,919,975 A | * | 11/1975 | Duncan | .................... 119/14.05 |
| 4,016,832 A | * | 4/1977 | Kiestra | .................... 119/14.14 |
| 4,452,176 A | * | 6/1984 | Hoefelmayr et al. | ..... 119/14.17 |
| 5,743,209 A | * | 4/1998 | Bazin et al. | ............. 119/14.08 |
| 5,865,138 A | * | 2/1999 | van der Lely | ........... 119/14.02 |
| 5,881,669 A | * | 3/1999 | van den Berg et al. | ... 119/14.03 |
| 5,957,081 A | * | 9/1999 | van der Lely et al. | .... 119/14.09 |

(Continued)

FOREIGN PATENT DOCUMENTS

DE    1773656    8/1972

(Continued)

OTHER PUBLICATIONS

First two pages of International Search Report published with PCT/SE 03/00651 listing documents considered relevant.

(Continued)

*Primary Examiner*—Yvonne R. Abbott
(74) *Attorney, Agent, or Firm*—Hovey Williams LLP

(57) ABSTRACT

This invention relates to a device and a method for sampling of milk. The device includes a collecting member (15, 15') arranged to receive milk samples from a milk line (1), which is arranged to transport milk from one animal (3) at a time, and a passage (8*a*, 12", 13) arranged to allow a milk flow from the milk line (1) to the collecting member (15, 15'). The device comprises flow means (11, 19) arranged to provide a milk flow, from the animal (3), through at least a part of the passage (8*a*, 12", 13) at least a time period before a milk sample is to be taken in order to rinse at least the part of the passage (8*a*, 12", 13) from milk residues from a previously milked animal.

29 Claims, 5 Drawing Sheets

U.S. PATENT DOCUMENTS

| | | | |
|---|---|---|---|
| 6,038,030 A * | 3/2000 | van den Berg | 356/425 |
| 6,694,830 B2 * | 2/2004 | Hakes | 73/863.53 |
| 6,725,803 B2 * | 4/2004 | Van der Lingen et al. | 119/14.02 |
| 6,814,025 B2 * | 11/2004 | Chen et al. | 119/14.01 |
| 6,971,330 B2 * | 12/2005 | Nilsson | 119/14.02 |

FOREIGN PATENT DOCUMENTS

| | | |
|---|---|---|
| DE | 2354820 | 11/1974 |
| EP | 0098966 | 1/1984 |
| EP | 0564023 | 12/1993 |
| EP | 0713641 | 5/1996 |
| FR | 2645705 | 10/1990 |
| SE | 0515093 | 6/2001 |
| WO | WO 9215196 | 9/1992 |
| WO | WO 2004/057305 A2 | 7/2004 |

OTHER PUBLICATIONS

Copy of GB 2 231 658: English language patent family member of FR 2645705 to serve as translation of same.
Abstract in English of EP 0098966.
Abstract in English of SE 515 093.

* cited by examiner

DEVICE AND A METHOD FOR SAMPLING OF MILK

THE BACKGROUND OF THE INVENTION AND PRIOR ART

The present invention relates to a device and a method for sampling of milk from an animal the milk of which is to be tested, wherein the device comprises a collecting member arranged to receive milk samples from a milk line, which is arranged to transport milk from one animal at a time, and a passage arranged to allow a milk flow from a milk line to the collecting member.

Sampling of milk is performed in order to analyse the quality of the milk. Thereby, the content of particular substances and the existent of bacterium in the milk of individual cows may be analysed. Usually, tubes having a relative small inner diameter are used for delivering milk samples from a milk line to a milk analysing device. Inevitably, milk residues from previous samplings are stored as a thin film along the inner walls of such tubes. Thereby, the amount of milk forming this film is not negligible in relation to the whole amount of milk in a sample. Consequently, the risk is obvious that milk samples conveyed in such tubes comprise a relatively high percentage of milk from previously milked cows. Thereby, the result of the analysis of a milk sample from a specific cow may be influenced of milk from previously milked cows.

Somatic cell count (SCC) defines the number of white cells per millilitre of milk. SCC scores are used as an international standard in determining the quality and the price of the milk. In order to determine the number of somatic cells in a milk sample, it is extremely important that the milk sample does not contain milk residuals from the previously milked cow, so-called carry over. In such a case, the measurement result could be completely incorrect. In an automatic milk arrangement, it is a desired to provide an automatic analysis of the number of somatic cell in the milk from individual cows. In this case, it is a problem to provide a quick and effective washing of the passage, through which milk samples are delivered to a milk analysing device.

WO 92/15196 shows an apparatus for sampling of milk from a milk line. The apparatus comprises a by-pass line comprising a pump, a timer, a sampling valve, and a test actuator. A milk flow is obtained in the by-pass line during a test period when the timer is set in a position, which initiates activation of the pump. Thus, a milk flow through the by-pass is here obtained during the sampling time period. There is a big risk that milk residues from a previous milked cow in the by-pass line are mixed with the milk sample of the cow, which is to be tested. In an embodiment of this invention, the milk is guided into the by-pass line via an inlet opening in a collector. After the milk has passed through the by-pass line, it is guided back to the milk line, via an outlet opening, to the collector. The outlet opening in the collector is positioned at a small distance downstream of the inlet opening. Especially at a low milk flow in the milk line, it is an obvious risk that milk from different cows is mixed in the collector and milk from previously milked cows is guided back into the inlet opening of the by-pass line.

DE 23 54 820 shows a milk line having an extension between a first container and a second container. A conduit has an extension between these containers in parallel with the ordinary milk line. A sampling device is arranged to allow sampling of the milk in the conduit. The sampling device, which has a relatively complex construction, is arranged to discharge milking samples from the conduit, via a branch conduit, to a sample container.

SUMMARY OF THE INVENTION

The object of the present invention is to provide a sampling device and a method, which provide reliable milk samples from individual animals without influences of possible milk residues stored in the conduit arrangement from previously milked animals.

This object is achieved in that the device comprises flow means arranged to provide a flow of milk, from said animal, through at least a part of the passage at least a time period before a milk sample is taken in order to rinse at least said part of the passage from milk residues from a previously milked animal. Such a milk flow in the passage removes relatively quickly possible residues of milk from a previously milked animal in the conduit. Thereby, the risk that such milk residues will affect a milk sample of the milk from the milked animal is substantially eliminated. Such a rinsing process of the passage is very simple and it does not require a disconnection of the conduit arrangement from the milk line. The rinsing process does not remain any residue of water or another cleaning liquid into the conduit, which may affect the milk sample. Consequently, a drying process in order to remove such water or a cleaning liquid from the passage is also unnecessary. Hence, the rinsing process does not affect the milking process at all. The milk line may comprise a collecting container, wherein the passage is arranged to allow a milk flow from the collecting container to the collecting member. Such a temporarily collecting container may be used to store the milk in the milk line from the tested animal until the result of the sampling is obtained. If the milk quality is satisfactory, the milk is transported to a larger milk container collecting milk from several cows. If the milk quality is not satisfactory, the milk in the temporarily collecting container is discarded.

According to a preferred embodiment of the invention, the device comprises a conduit loop, having a first end connected to a milk line and a second end connected to the milk line at a distance from the first end, wherein at least a first part of the conduit loop, is comprised in said passage. An analysis device requires a relatively great deal of space. By using such a conduit loop, the length of the tube, which transports the milk samples to the analysis device, may be reduced. The second end of the conduit loop, which comprises an outlet opening, is thus connected to the milk line at a distance downstream of the first end, which comprises the inlet opening. Thereby, the milk, which has passed through the conduit loop, is prevented to return into the inlet opening. The milk flow through the conduit loop may rinse said first part of the conduit. Said milk is then guided back to the milk line. The rinsing process achieved by the milk from the animal, which is milked, is simple, quick, and effective.

Advantageously, the first part of conduit loop has an extension from the first end to a valve member, which is arranged to allow a discharge of the milk in the conduit loop to the collecting member. Such a valve member may be a three-way valve. The device may comprise a second conduit, having an extension from the valve member to the collecting member, which second conduit comprises a second part of the passage. In most cases, it is necessary to use a short such a second conduit in order to transport the milk from the conduit loop to the collecting member. However, this second part of the passage is preferably much shorter than the first part of the passage. Advantageously, a milk flow from said animal is also arranged to flow through the second part of the passage in order to rinse it from milk residues from previously milked animals. Thereby, the whole passage is rinsed by milk from the animal to be milked and the affect of a milk sample from previously milked animals is substantially eliminated.

According to an alternative embodiment of the invention, the first part of conduit loop has an extension from the first end of the conduit loop to a collecting member, which is arranged in the conduit loop. In this case, the milk sample may be collected in a collecting container also called measurement chamber. Advantageously, the conduit loop may comprise a valve, which in a closed position is arranged to accomplish stagnant milk in the collecting member. The most milk analysis devices require that the milk in the sample is stagnant during the analysis. Alternatively, the device may comprise a valve arranged in the milk line, wherein said passage comprises at least an opening of the valve. In this case, a very short passage is obtained, which has to be rinsed by milk.

According to a preferred embodiment of the invention, the flow means is arranged to provide said milk flow in at least said part of the passage as soon as milk from said animal flows in the milk line at the first end of the conduit loop. Thereby, the rinsing process starts as soon as it is possible to use milk from the milked animal to rinse the passage. After, for example, a determined time period or after that a determined amount of the milk has passed through the valve member, a sample of the milk may be taken. The flow means may comprise a pump, which could be arranged in the first part of the passage. By using such a pump, a rinsing milk flow in the passage is guaranteed. Alternatively, the flow means may comprise the gravitation or the pressure difference between the ends of the conduit loop.

According to another preferred embodiment of the invention, the device may comprise an analysing device. The analysing device is arranged to analyse the quality of the milk in the sample. Thereby, the content of particular substances and the existent of bacterium in the milk sample may be analysed. The flow means may comprise a pump arranged in the analysing device. Thereby, when the three-way valve allows a milk flow through the second conduit, the pump sucks the milk from the milk line into the passage to the collecting member. Thereby, the flow of the milk sample from the milk line to the analysing device is guaranteed. The analysis device may be arranged to count somatic cells or fat droplets in the milk sample. The number of somatic cells in the milk sample is an important parameter in order to determine the quality of the milk. Such an analysis device may be arranged to add chemical substances to the milk sample in order to count the somatic cells or fat droplets in the milk sample. This method is simple, low cost and quick. Alternatively, the analysing device is arrange to use a camera system to record images of the milk sample in the collecting member in order to count somatic cells and/or fat droplets. Such a method is possible to use in an automatic milking arrangement and it provides a counting of the somatic cells or fat droplets in the milk sample with a high degree of accuracy.

According to another preferred embodiment of the invention, the device may comprise a control unit arranged to control the milk sampling process. Such a control unit may be a computer device. Thereby, automatic milk sampling of individual animals may be performed. The control unit may be arranged to initiate sampling of the milk only after that a certain amount of milk from said animal has passed through at least said part of the passage. Such an amount is the estimated amount for rinsing the first part of the passage from milk residues from a previously milked animal. The control unit may be able to control the activation of said flowing means. The control unit may for example, be able to switch the three-way valve to the first position, in which a milk flow is guided through the whole conduit loop, and to a second position, in which a milk flow is guided from the first end of the conduit loop to the collecting member in the analysing device. The control unit may keep the three-way valve in the second position during a time period such that a suitable amount of milk from the conduit loop is guided to the second conduit. The initial part of the milk flow in the second conduit is used to rinse the passage and the final part of the milk flow is collected in the collecting member as a milk sample.

According to another preferred embodiment of the invention, the control unit is connected to a reading device and arranged to receive information from the reading device about the identity of the animal. In an automatic milking and sampling device such an information is necessary in order to relate a milk sample to a specific animal. The control unit may be connected to a flow meter and arranged to receive information from the flow meter about the presence of a milk flow in the milk line. With such information, the control unit may control the activation of the pump in the first part of the passage or the activation of the pump in the analysis device. Thereby, the pump may be started, as soon as a milk flow is present in the milk line and stopped as soon as the milk flow has ended in the milk line. Alternatively, the pump may be driven substantially continuously. The control unit may be connected to the analysing device and be arranged to receive information from the analysing device about the results of the milk samples. Thereby, the control unit may store the result of the analysed milk sample. The control unit may also have the possibility to control a removing unit, which removes the milk from a specific animal if the milk sample discloses that the quality of the milk is not sufficiently high. The milk from a specific animal may be stored temporarily in a collecting container until the control unit receives information about the quality of the milk from the analysing device.

According to another preferred embodiment of the invention, the conduit has a smaller inner cross-section area than the milk line. The conduit may, for example, have a diameter of about 2 mm. Thereby, only a relatively small amount of the milk in the milk line needs to be sucked into the conduit. The device may be connected to a milk line arranged to transport milk from one teat of an animal at a time. Thereby, an infected teat of an animal may be detected and the milk from such a teat discarded.

According to another preferred embodiment of the invention, the device is connected to a milk line, which constitutes a part of an automatically controlled arrangement for milking of animals. In automatic milking arrangements it is desirable to provide an automatic sampling of the quality of the milk from individual animals and from theirs individual teats. The arrangement may comprise a milking robot, which is arranged to attach teat cups to the individual teats of the animal. Such a milking robot may comprise a device for sampling of milk from an animal, the milk of which is to be tested, wherein the device comprises a collecting member arranged to receive milk samples from a milk line, which is arranged to transport milk from one animal at a time, a passage arranged to allow a milk flow from the milk line to the collecting member, and an analysing device arranged to count somatic cells and/or fat droplets in the milk sample.

Furthermore, the milking robot comprises flow means arranged to provide a milk flow, from said animal, through at least a part of the passage at least a time period before a milk sample is taken in order to rinse at least said part of the passage from milk residues from a previously milked animal. Consequently, the milk sampling device may constitute an integrated part of the milking robot.

The invention also relates to a method for sampling of milk from an animal, the milk of which is to be tested, wherein a device is used comprising a collecting member arranged to receive milk samples from a milk line, which is arranged to transport milk from one animal at a time, and a passage arranged to allow a flow of milk from the milk line to the collecting member. The method is characterised by the step of: providing a milk flow from said animal through at least a part of the passage at least a time period before a milk sample is taken in order to rinse at east said part of the passage from milk residues from a previously milked animal. The initial milk flow from said animal removes effectively possible residues of milk from previously milked animals in the passage. Thereby, the risk that a milk sample is mixed with milk from previously milked animals is substantially eliminated. Consequently, an effective rinsing process of the passage from milk residuals is obtained in a quick and simple way.

BRIEF DESCRIPTION OF THE DRAWINGS

The present invention is now to be explained more closely by means of a preferred embodiment, which is disclosed as an example, and with reference to the attached drawings.

DETAILED DESCRIPTION OF PREFERRED EMBODIMENTS OF THE INVENTION

Figure 1:
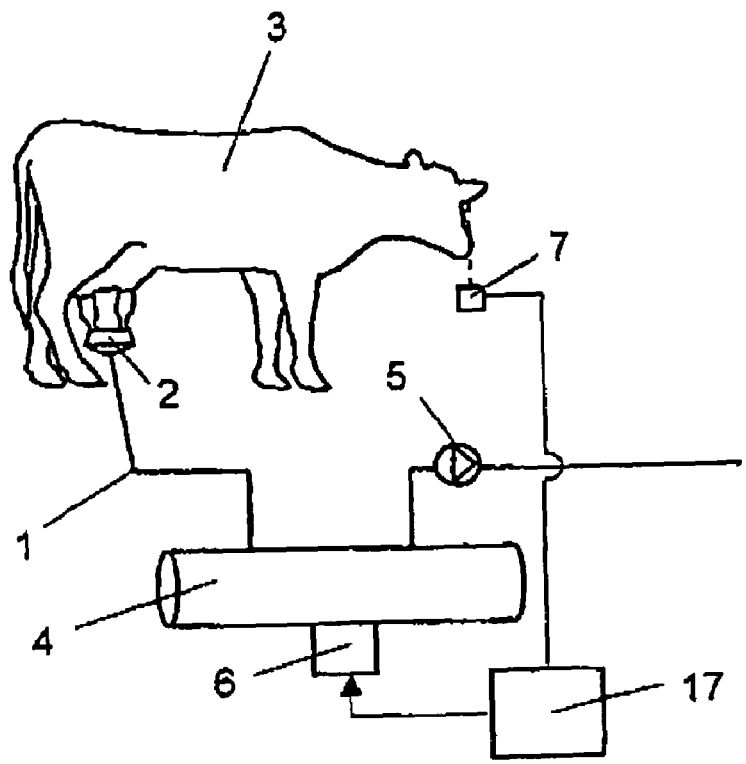
FIG. 1 shows a milk line with a first embodiment of a device for sampling of milk.

FIG. 1 shows a milk line 1 having an extension from a claw 2, which is attachable to a cow 3 during a milking process. The milk line 1 comprises a collecting container, in the form of an end unit 4. The end unit 4 is arranged to store the milk from the cow 3 temporarily. A vacuum pump 5 guarantees the transport of the milk to the end unit 4. A sampling device 6 is connected to the end unit 4, for allowing sampling of the milk in the end unit 4. Since the milk line 1 has an extension from only one claw 2, the milk in the milk line 1 originates from one cow 3 at a time. In order to identify the milked cow 3, a reading device 7 is arrange to read a specific code from a transponder, which, in this case, is attached to an ear of the cow 3. The sampling device 6 is arranged to discharge a small amount of the milk collected in the end unit 4 as a milk sample through a passage. According to the invention, the device 6 is arranged to provide a milk flow, through said passage at least a time period before a milk sample is taken in order to rinse the passage from milk residues from a previously milked animal. Thereafter, the sampling device 6 is arranged to analyse the quality of the milk. A control unit 17 is arranged to supervise and control the milk sampling device 6 and the milk sampling process. Such a control unit 17 comprises a computer having suitable software for this purpose. By using such a control unit 17, an automatic sampling of the milk from individual cows 3 is possible to accomplish.

Figure 2:
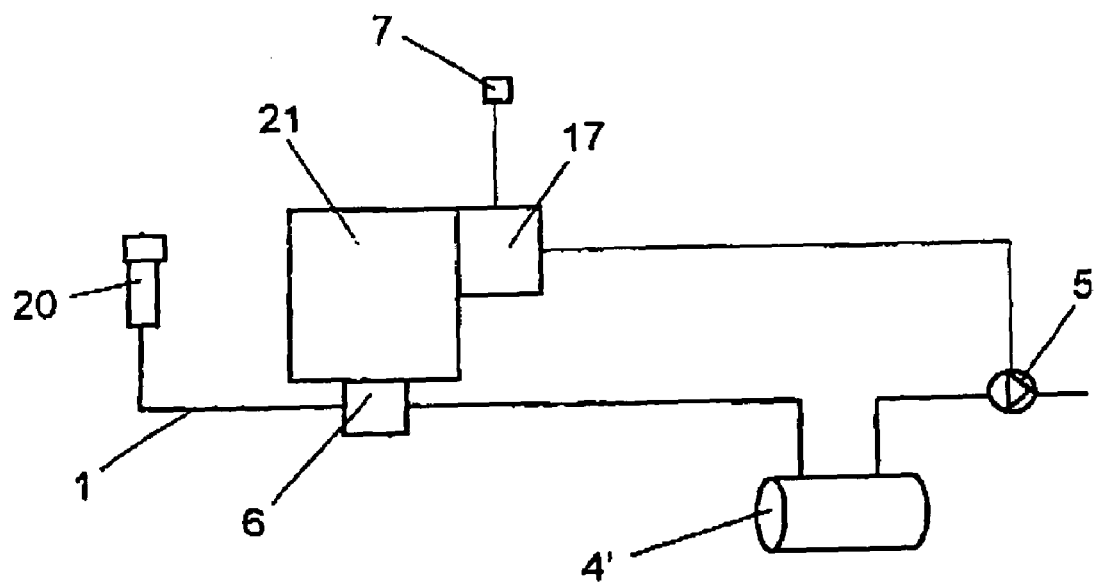
FIG. 2 shows an alternative milk line with a second embodiment of a device for sampling of milk.

FIG. 2 shows a milk line 1 having an extension from a teat cup 20, which is attachable to a cow 3 during a milking process. The milk line 1 comprises here a collecting container, in the form of a sub end unit 4'. In reality, there is four parallel milk lines 1, which each extent from a teat cup 20. The four milk lines 1 comprises each a sub end unit 4', which is arranged to store the milk from the respective teats of a cow 3 temporarily. The four sub end units 4' may constitute integrated parts of one end unit 4. A vacuum pump 5 guarantees the transport of the milk to the respective sub end units 4'. A sampling device 6 is connected to the milk line 1. The sampling device 6 is arranged to discharge a small amount of the milk from the milk line 1 as a milk sample through a passage. According to the invention, the device 6 is arranged to provide a milk flow, through said passage at least a time period before a milk sample is taken in order to rinse the passage from milk residues from a previously milked animal.

The milk in the respective milk line 1 originates from one teat of a cow 3 at a time.

A schematically disclosed milking robot 21 is arranged to perform the attachment of the four teat cups 20 to a cow 3. The control unit 17 is arranged to receive information from the reading device 7 about the identity of the cow 3 and to control the milking robot 21, the pump 5, and the sampling device 6. Consequently, a substantially automatically controlled arrangement for milking and sampling is obtained. Since, the sampling device 6 here samples the milk from one teat of a cow 3, an infected teat of an animal may be detected. The milk from said teat, which is temporarily collected in the sub end unit 4' will be discarded. In this case, the sampling device 6 constitutes an integrated part of the milking robot 21. The control unit 17 may also be an integrated part of the milking robot 21.

Figure 3:
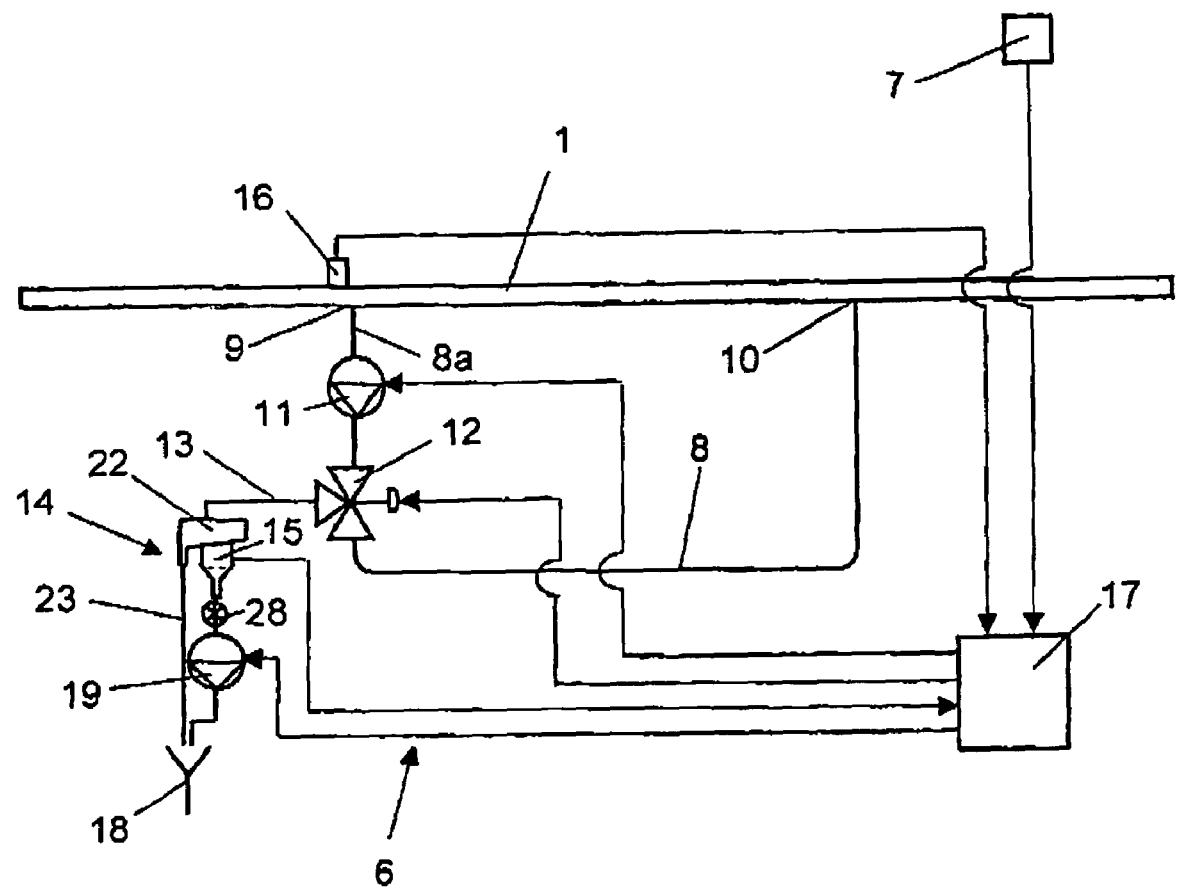
FIG. 3 shows a third embodiment of a device for sampling of milk.

FIG. 3 shows a third embodiment of a sampling device 6 according to the present invention. The sampling device 6 comprises a conduit loop 8 having an inlet opening at a first end 9, which is connected to the milk line 1, and an outlet opening at a second end 10. Thereby, a part of the milk, which flows in the milk line 1, is allowed to flow into the inlet opening at the first end 9 of the conduit loop 8. The milk in the conduit loop 8 is guided back to the milk line 1, via the outlet opening in the second end 10. Since the second end 10 is connected to the milk line 1 at a distance downstream of the first end 9, the milk, which has passed through the conduit loop 8, is prevented to return to the conduit loop 8. The conduit loop 8 has a substantially smaller inner cross-section area than the milk line 1. Thereby, only a relatively small amount of the milk, which flows in the milk line 1, is sucked into the conduit loop 8.

A pump 11 and a three-way valve 12 are arranged in the conduit loop 8. The pump 11 is positioned in a first part 8a of the conduit loop 8, which first part 8a has an extension from the first end 9 to the three-way valve 12. The three-way valve 12 is mostly positioned in a first position, in which it allows the milk to pass through the valve 12 in a direction towards the outlet opening 10. When the control unit 17 initiates that a milk sample is to be taken, the three-way valve 12 is switched to a second position. In the second position the three-way valve 12 discharges the milk flow from the first part of conduit loop 8a to a second conduit 13, which guides the milk to a milk analysing device 14. The milk analysing device 14 is here arranged to count somatic cells or fat droplets in the milk. The analysing device 14 comprises a collecting member, in the form of a delivery funnel 15, which is arranged to collect the milk to be analysed. The delivery funnel 15 comprises at the top an overflow member 22, which restricts the amount of the milk in the delivery funnel 15. The surplus amount of milk is guided, via a sewer conduit 23, to an outlet conduit 18. A pump 19 is arranged to drain the milk from the delivery funnel 15 when a valve 28 is open.

Consequently, the milk to be sampled is transported through a passage, which has an extension from the milk line 1 to the delivery funnel 15. This passage comprises the first part 8a of the conduit loop 8 and the second conduit 13. A flow meter 16 is arranged in the milk line 1 in order to measure the flow rate in the milk line 1. The control unit 17 is arranged to supervise and control the milk sampling process. By using a control unit 17, a substantially automatic sampling of the milk from individual cows 3 is possible to accomplish.

When a cow 3 has entered, for example, a milking stall, a milking robot 21 attaches the teat cups 20 to the cow 3. The reading device 7 reads the identity of the cow 3 and informs the control unit 17 about the identity of the cow 3 by a signal. The milking process starts and the milk from the cow 3 begins to flow in the milk line 1. The milk in the milk line 1 is transported by the vacuum pump 5 in a direction towards a collecting container in the form of a sub end unit 4'. The respective teat cups 20 are connected to a respective sub end unit 4'. The flow meter 16 detects the milk flow in the milk line 1. The flow meter 16 informs the control unit 17 by a signal about the presence of the flow and the flow value in the milk line 1. The control unit 17 initiates activation of the pump 11, which establishes a negative pressure at the first end 9 of the conduit loop 8. Thereby, a part of the milk, which flows In the milk line 1, is sucked into the conduit loop 8, via the inlet opening, at the first end 9.

The milk flow, from the cow 3, removes possible milk residues in the conduit loop 8 from the previously milked cow. Such milk residues may be stored as a thin film along the inner wall surface of the conduit loop 8. The milk from the cow, which is milked, provides a very simple, quick and effective rinsing of the conduit loop 8 from milk residues. Thereby, remaining milk residues in the first part 8a of the conduit loop 8 will not influence on a milk sample of the presently milked cow 3. The control unit 17 initiates sampling of the milk from the cow 3 only after that a time period has passed and/or a suitable amount of milk from the cow 3 has flown through the three-way valve 12 in the conduit loop 8. When, such a suitable amount of milk has flown through the three-way valve 12, the risk that milk residues from the previously milked cow remains in the first part 8a of the conduit loop 8 is substantially eliminated.

When a sample of the milk from the cow 3 is to be taken, the control unit 17 initiates an adjustment of the three-way valve 12 from the first position to the second position. The milk in the first part 8a of the conduit loop 8 is now directed into the second conduit 13. The valve 28 is open and the pump 19 is activated such that the milk, which enters the delivery funnel 15, is drained out through the outlet conduit 18. The outlet conduit 18 may transport this milk back to the conduit loop 8 downstream of the three-way valve 12 or to a specific container for milk to be discarded. Thereby, the initial milk flow through the second conduit 13 removes milk residues in the second conduit 13 from a previously tested cow. Consequently, the milk rinses the first part 8a of the conduit loop and the second conduit 13 from milk residues. However, the delivery funnel 15 is washed in a conventional manner between each sampling. When a determined amount of milk has passed the delivery funnel 15, the valve 28 is closed and the drain pump 19 is stopped. The milk flow in the second conduit 13 fills now the delivery funnel 15. When the delivery funnel 15 is filled with milk, a quantity of milk is sucked from the delivery 15 to a test tube. Chemical substances are added to the test tube. The colour change of the milk in the test tube makes it possible to indicate the number of somatic cells in the milk sample. The control unit 17 receives a signal from the analysis devices 14 about the result of the sampling. Then, the control unit 17 opens the valve 28 and activates the pump 19 such that the milk in the delivery funnel 15 is drained out through the outlet conduit 18.

By information about the flow value in the milk line 1, the control unit 17 may keep the three-way valve 12 in the second position at a time period such that a desired amount of milk for rinsing and for sampling is delivered through the second conduit 13. After that a milk sample has been taken, the three-way valve 12 is switched back to the first position. The control unit 17 stores the received information about the quality of the milk from the cow 3. The milk may be stored in the sub end unit 4' until the control unit 17 has received information about the quality of the milk from the analysing device 14. If the milk from said teat of the cow 3 does not perform determined requirements of the quality, the milk in the sub end unit 4' is discarded.

Figure 4:
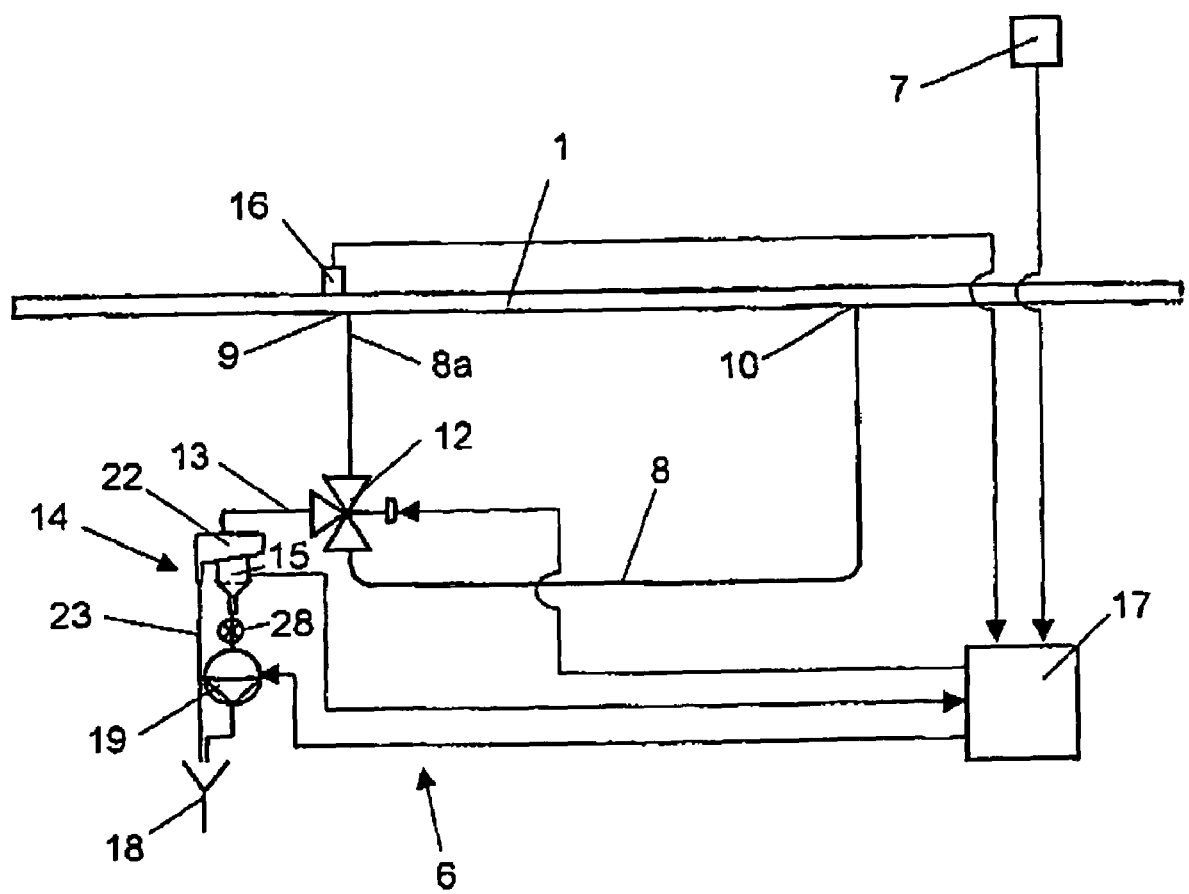
FIG. 4 shows a fourth embodiment of a device for sampling of milk.

FIG. 4 shows a fourth embodiment of the device. When the three-way valve 12 here is in the first position, the gravitation and/or the pressure difference between the first end 9 and the second end 10 of the conduit loop 8 are arranged to provide a continuous milk flow in the conduit loop 8. This flow arises as soon as milk flows in the milk line 1 at the first end 9 of the conduit loop 8. Thereby, a quick and effective rinsing of milk residues from the previously milked cow is achieved in the first part 8a of the conduit loop 8. When a sample of the milk from the cow 3 is to be taken, the control unit 17 initiates an adjustment of the three-way valve 12 from the first position to the second position. The control unit 17 opens the valve 28 and activates the pump 19 in the analysing device 14. The milk in the first part 8a of the conduit loop 8 is now sucked into the second conduit 13 by the pump 19. The initial milk flow in the second conduit 13 streams through the analysing device 14 and out through the outlet conduit 18. The outlet conduit 18 may transport this milk back to the conduit loop 8 downstream of the three-way valve 12 or to a storage container for milk to be discarded. Thereby, the initial milk flow removes possible milk residues from the previously milked cow in the second conduit 13. When a determined amount of milk has passed the second conduit 13, the valve 28 is closed and the drain pump 19 is stopped. The final milk flow through the second conduit 13 fills the delivery funnel 15.

By information about the flow rate in the milk line 1, the control unit 17 may keep the three-way valve 12 in the second position at a time period such that a desired amount of milk for rinsing and for sampling is delivered through the second conduit 13. The three-way valve 12 is then switched back to its first position. The control unit 17 receives information about the results from the analysing device 14. The control unit 17 stores the received results about the quality of the milk from the cow 3. The milk may be stored temporarily in an end unit 4 until the control unit 17 receives the results from the analysing device 14. If the milk from the cow 3 does not perform determined requirements of the quality, the milk in the end unit 4 is discarded.

Figure 5:
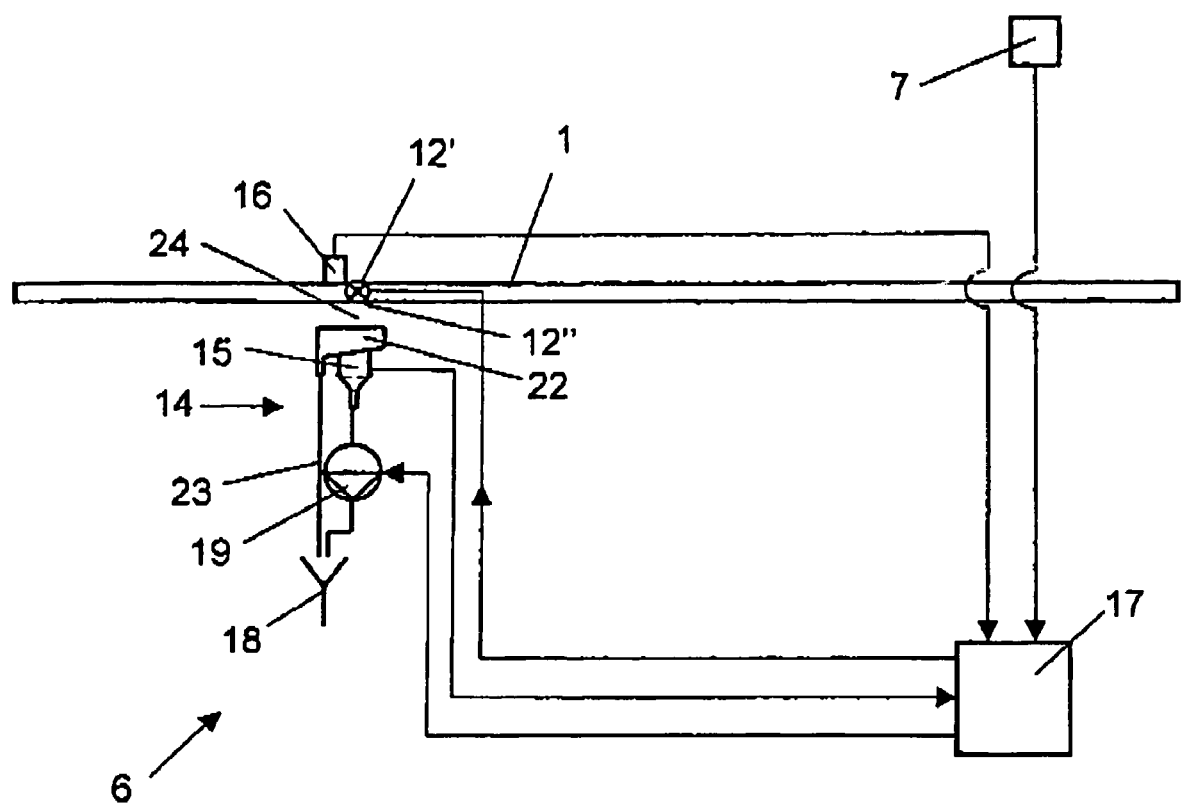
FIG. 5 shows a fifth embodiment of a device for sampling of milk and FIG. 6 shows a sixth embodiment of a device for sampling of milk.

FIG. 5 shows a fifth embodiment of the device. In this case a valve 12' is arranged in the milk line 1. The valve 12' is arranged to allow a discharge of milk samples substantially direct from the milk line 1. The valve 12' comprises a closeable opening 12" located at a bottom surface of the milk line 1. An analysis device 14 is arranged in a position straight below said opening 12" of the valve 12'. The control unit 17 is arranged to set the valve 12' in an open position when a milk sample is to be taken. An air gap 24 is arranged between the valve 12' and the analysis device 14. When a sample of the milk from a cow 3 is to be taken, the control unit 17 sets the valve 12' in an open position. Thereby, a smaller part of the milk in the milk line 1 is discharged through said opening 12" and into the delivery funnel 15 of the analysis device. The initially discharged milk flows through the delivery funnel 15 and out through the outlet conduit 18. The outlet conduit 18 may transport this milk back to the milk line 1 downstream of the valve 12' or to a storage container for milk to be discarded. Thereby, the initial milk flow removes possible milk residues from a previously milked cow 3 from at least the surface, which defines the opening 12" of the valve, When a determined amount of milk has been discharged from the milk line 1, the valve 28 is closed and the drain pump 19 is stopped. The final discharged milk from the milk line 1 flow through the opening 12" of the valve 12' and fills the delivery funnel 15. In this case, the passage is very short. The passage is defined substantially only by the opening 12" of the valve 12'. The flow means is here the gravitation.

Figure 6:
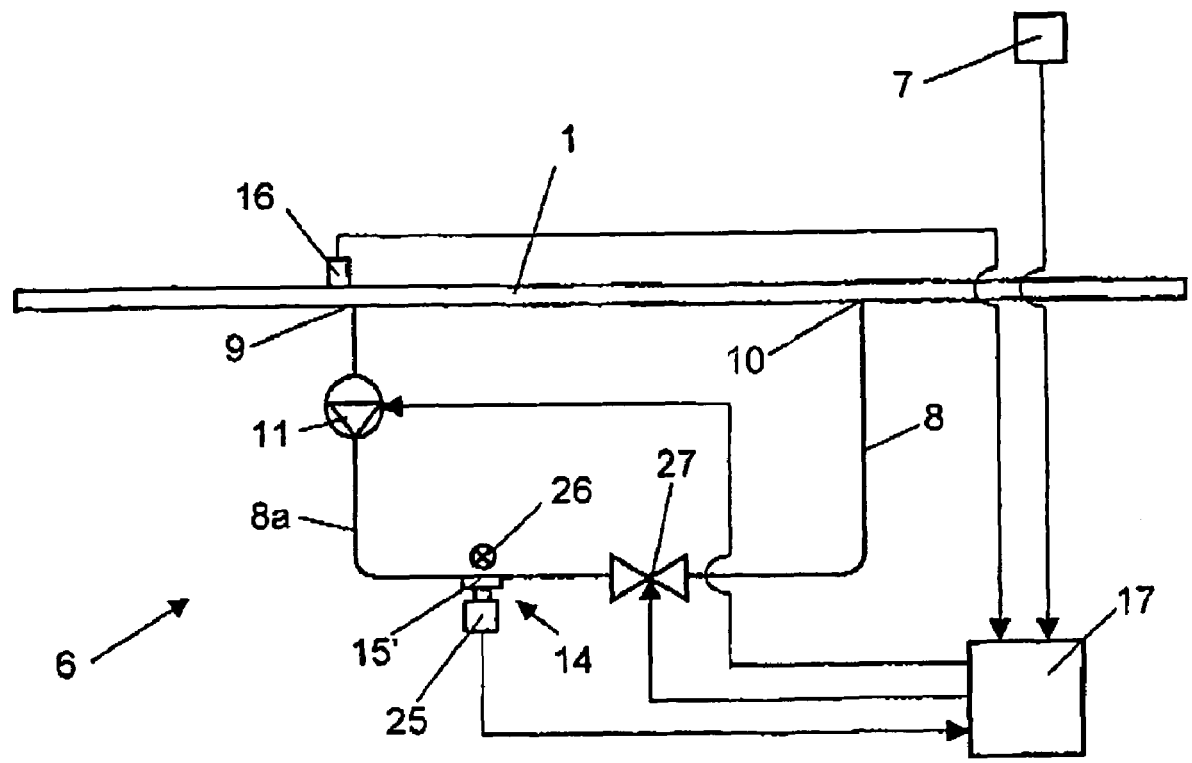

FIG. 6 shows a sixth embodiment of the device. In this case, the conduit loop 8 comprises a collecting chamber in the form of a flat measuring chamber 15'. Transparent walls define the measuring chamber 15' at least partly. A camera apparatus 25 is arranged at one wall surface of the measuring chamber 15' and a light source 26 is arranged at the opposite wall of the measuring chamber 15'. A two-way valve 27 is arranged downstream of the measuring chamber 15' in the conduit loop 8.

When a sample of the milk in a milk line 1 is to be taken, the control unit 17 initiates activation of the pump 11 such that a milk flow is obtained in the conduit loop 8. The control unit 17 sets the two-way valve 27 in an open position. Thereby, the milk flows through a first part 8a of the conduit loop 8, which is located before the measuring chamber 15', through the measuring chamber 15' and through the remaining part of the conduit loop 8 back to the milk line 1. Thereby, the milk flow removes milk residues from a previously milked cow in the conduit loop 8. When a determined amount of milk has passed through the first part 8a of the conduit loop, the pump 11 is stopped and the two-way valve 27 is set in a closed position. Thereby, the milk in the measurement chamber 15' becomes stagnant. The camera apparatus 25 may comprise a microscope such that images of the stagnant milk in a small area of the measuring chamber 15' may be recorded. In this area, the measuring chamber 15' may have a thickness of about 0, 1 mm. By recording a large number of images and by means of digital processing of these images, a somatic cell count score can be determined.

After that a milk sample has been taken, the control unit 17 activates the pump 11 and sets the two-way valve 27 in an open position. The control unit 17 stores the received information about the somatic cell count score of the milk. The milk from the cow 3 may be stored in the end unit 4 until the control unit 17 has received and ascertained the result of the milk sample. If the milk from the cow 3 does not perform determined requirements of the quality, the milk in the end unit 4 may be removed as no usable.

The invention is not restricted to the described embodiments of the invention but may be varied freely within the scope of the claims.

The invention claimed is:

1. A device for sampling of milk from an animal, the milk of which is to be tested, wherein the device comprises:
   a collecting member arranged to receive milk samples from a milk line, which is arranged to transport milk from one animal at a time; and
   a passage arranged to allow a milk flow from the milk line to the collecting member;
   wherein the device further comprises flow means arranged to provide a milk flow, from the animal, through at least a part of the passage at least a time period before a milk sample is taken in order to rinse at least said part of the passage from milk residues from a previously milked animal;
wherein the device further comprises a conduit loop having a first end connected to the milk line and a second end connected to the milk line at a distance from the first end, wherein at least a first part of the conduit loop is comprised in said passage.

2. A device according to claim 1, wherein the milk line comprises a collecting container, wherein the passage is arranged to allow a milk flow from the collecting container to the collecting member.

3. A device according to claim 1, wherein the first part of conduit loop has an extension from the first end to a valve member, which is arranged to allow a discharge of the milk in the conduit loop to the collecting member.

4. A device according to claim 3, wherein the valve member comprises a three-way valve.

5. A device according to claim 3, wherein the device further comprises a second conduit having an extension from the valve member to the collecting member, which second conduit constitutes a second part of the passage.

6. A device according to claim 1, wherein the first part of conduit loop has an extension from the first end of the conduit loop to a collecting member which is arranged in the conduit loop.

7. A device according to claim 6, wherein the conduit loop comprises a valve, which in a closed position is arranged to accumulate stagnant milk in the collecting member.

8. A device according to claim 1, wherein the device further comprises a valve arranged in the milk line, wherein passage comprises at least an opening of the valve.

9. A device according to claim 1, wherein said flow means is arranged to provide the milk flow in at least said part of the passage as soon as milk from the animal flows in the milk line at the first end of the conduit loop.

10. A device according to claim 1, wherein the flow means comprises a pump.

11. A device according to claim 1, wherein the milk flow provided by the flow means is gravity aided.

12. A device according to claim 1, wherein the device further comprises an analysing device, which is arranged to analyse the milk in the collecting member.

13. A device according to claim 12, wherein the analysing device is arranged to provide a count from the group consisting of somatic cells, fat droplets, and combinations thereof, in the milk sample.

14. A device according to claim 13, wherein the analysing device is arranged to add chemical substances to the collecting member in order to provide the count of the group consisting of somatic cells, fat droplets and combinations thereof in the milk sample.

15. A device according to claim 13, wherein the analysing device is arranged to use a camera system to record images of the milk sample in the collecting member in order to provide the count from the group consisting of somatic cells, fat droplets, and combinations thereof.

16. A device according to claim 1, wherein the device further comprises a control unit arranged to control the milk sampling process.

17. A device according to claim 16, wherein the control unit is arranged to initiate sampling of the milk only after that a certain amount of milk from the animal has passed through at least said part of the passage.

18. A device according to claim 16, wherein the control unit is arranged to control the activation of said flow means.

19. A device according to claim 16, wherein the control unit is connected to a reading device and arranged to receive information from the reading device about the identity of the animal.

20. A device according to claim 16, wherein the control unit is connected to a flow meter and arranged to receive information from the flow meter about the presence of a milk flow in the milk line.

21. A device according to claim 16, wherein the control unit is connected to an analysing device and arranged to receive information from the analysing device about the results of the milk samples.

22. A device according to claim 1, wherein the conduit loop has a smaller inner cross-section area than the milk line.

23. A device according to claim 1, wherein the device is connected to a milk line, which is arranged to transport milk from one teat of an animal at a time.

24. A device according to claim 1, wherein the device is connected to a milk line, which constitutes a part of an automatically controlled arrangement for milking of animals.

25. A device according to claim 24, wherein the arrangement comprises a milking robot.

26. A milking robot comprising a device according to claim 1, wherein the device constitutes an integrated part of a milking robot.

27. A method for sampling of milk from an animal, the milk of which is to be tested, comprising the steps of:
providing a device comprising a collecting member arranged to receive milk samples from a milk line which is arranged to transport milk from one animal at a time, and a passage arranged to allow a milk flow from the milk line to the collecting member, said device further including a conduit loop having a first end connected to the milk line and a second end connected to the milk line at a distance from the first end, at least a first part of the conduit loop is comprised in the passage, said method further comprising the step of:
providing a milk flow from the animal through at least a part of the passage at least a time period before a milk sample is taken in order to rinse at least said part of the passage from milk residues from a previously milked animal, wherein at least a part of the milk flow from the animal flows into the first end of the conduit loop.

28. A method for collecting milk from an animal comprising the step of milking an animal using an arrangement for the milking of animals which includes a device according to claim 1.

29. A milking robot, wherein the milking robot comprises a device for sampling of milk from an animal the milk of which is to be tested, a collecting member arranged to receive milk samples from a milk line , which is arranged to transport milk from one animal at a time, a passage arranged to allow a milk flow from the milk line to the collecting member, and an analysing device arranged to provide a count of the group consisting of somatic cells, fat droplets, and combinations thereof in the milk sample, wherein the milking robot comprises flow means arranged to provide a milk flow, from the animal, through at least a part of the passage at least a time period before a milk sample is taken in order to rinse at least said part of the passage from milk residues from a previously milked animal,
wherein the device further comprises a conduit loop having a first end connected to the milk line and a second end connected to the milk line at a distance from the first end, wherein at least a first part of the conduit loop is comprised in said passage.

* * * * *